(12) United States Patent
Shen

(10) Patent No.: US 11,119,172 B2
(45) Date of Patent: Sep. 14, 2021

(54) SYSTEMS AND METHODS FOR MAGNETIC RESONANCE IMAGING

(71) Applicant: SHANGHAI UNITED IMAGING HEALTHCARE CO., LTD., Shanghai (CN)

(72) Inventor: Zhenhua Shen, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 30 days.

(21) Appl. No.: 16/573,687

(22) Filed: Sep. 17, 2019

(65) Prior Publication Data

US 2020/0182954 A1    Jun. 11, 2020

(30) Foreign Application Priority Data

Dec. 7, 2018    (CN) .......................... 201811494140.3

(51) Int. Cl.
*G01V 3/00* (2006.01)
*G01R 33/54* (2006.01)
(Continued)

(52) U.S. Cl.
CPC .......... *G01R 33/543* (2013.01); *G01R 33/56* (2013.01); *G16H 30/20* (2018.01); *A61B 5/004* (2013.01);
(Continued)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS

| 8,571,288 | B2 * | 10/2013 | Sugiura | .............. | G01R 33/5635 |
| | | | | | 382/131 |
| 2009/0316465 | A1 * | 12/2009 | Jain | .......................... | G11C 7/22 |
| | | | | | 365/94 |

(Continued)

FOREIGN PATENT DOCUMENTS

| CN | 101904745 A | 12/2010 |
| CN | 102488519 A | 6/2012 |

(Continued)

OTHER PUBLICATIONS

First Office Action in Chinese Application No. 201811494140.3 dated Jul. 3, 2020, 18 pages.

*Primary Examiner* — Walter L Lindsay, Jr.
(74) *Attorney, Agent, or Firm* — Metis IP LLC

(57) ABSTRACT

A method for MRI may include obtaining one or more scan parameters. The one or more scan parameters may include information of a plurality of diffusion gradients. The method may include causing, based on the one or more scan parameters, an imaging device to perform a plurality of scans to one or more slices of an object by applying the plurality of diffusion gradients to the one or more slices. For two components in a specific direction of the plurality of diffusion gradients applied in any two successive scans of the plurality of scans, there may be at most one component exceeding a first threshold. The specific direction may be one of a readout direction, a phase-encoding direction, or a slice-selection direction. The first threshold may be less than diffusion gradient energy relating to a duration and strength associated with one of the plurality of diffusion gradients.

19 Claims, 11 Drawing Sheets

(51) Int. Cl.
*G16H 30/20* (2018.01)
*G01R 33/56* (2006.01)
*A61B 5/00* (2006.01)
*A61B 5/055* (2006.01)

(52) U.S. Cl.
CPC .......... *A61B 5/0042* (2013.01); *A61B 5/0044* (2013.01); *A61B 5/055* (2013.01)

(58) Field of Classification Search
USPC ....................................................... 324/309
See application file for complete search history.

(56) References Cited

U.S. PATENT DOCUMENTS

| 2015/0115960 A1* | 4/2015 | Grodzki | G01R 33/56341 |
| | | | 324/309 |
| 2017/0234956 A1* | 8/2017 | Feiweier | G01R 33/56341 |
| | | | 324/309 |

FOREIGN PATENT DOCUMENTS

| CN | 102631196 A | 8/2012 |
| CN | 107219484 A | 9/2017 |
| CN | 107536609 A | 1/2018 |

* cited by examiner

700

```
┌─────────────────────────────────────────┐
│ Obtaining one or more scan parameters,  │
│ wherein the one or more scan parameters │ ∼710
│ includes information of a plurality of  │
│ diffusion gradients                     │
└─────────────────────────────────────────┘
                    │
                    ▼
┌─────────────────────────────────────────┐
│ Causing, based on the one or more scan  │
│ parameters, an imaging device to        │
│ perform a plurality of scans to one or  │ ∼720
│ more slices of an object by applying    │
│ the plurality of diffusion gradients to │
│ the one or more slices                  │
└─────────────────────────────────────────┘
```

```
┌─────────────────────────────────────────────┐
│ Generating a first arrangement result by    │
│ ranking n diffusion gradients in a          │  ~810
│ descending order based on the components    │
│ in the readout direction of the             │
│ n diffusion gradients                       │
└─────────────────────────────────────────────┘
                      │
                      ▼
┌─────────────────────────────────────────────┐
│ Generating a second arrangement result      │  ~820
│ based on the first rank result              │
└─────────────────────────────────────────────┘
                      │
                      ▼
┌─────────────────────────────────────────────┐
│ Generating a third arrangement result by    │
│ filling the n diffusion gradients into a    │  ~830
│ list based on the second rank result        │
└─────────────────────────────────────────────┘
```

FIG. 8

SYSTEMS AND METHODS FOR MAGNETIC RESONANCE IMAGING

CROSS-REFERENCE TO RELATED APPLICATIONS

This application claims priority to Chinese Patent Application No. 201811494140.3 filed on Dec. 7, 2018, the contents of which are hereby incorporated by reference.

TECHNICAL FIELD

The present disclosure generally relates to systems and method for magnetic resonance imaging (MRI), and in particular, to systems and methods for diffusion imaging.

BACKGROUND

Diffusion imaging has been used extensively in clinical neurology, such as brain pathologies. In the diffusion imaging, one or more diffusion gradients are applied to generate contrast between an area of pathology and the surrounding healthy tissue. During a scanning process of the diffusion imaging, the amplifier in an MRI scanner works to generate not only encoding gradients but also diffusion gradients, which makes the workload of the amplifier higher. Therefore, it is desirable to provide systems and/or methods for the diffusion imaging to improve the stability of the amplifier during the scanning process of the diffusion imaging.

SUMMARY

According to a first aspect of the present disclosure, a system for MRI may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain one or more scan parameters. The one or more scan parameters may include information of a plurality of diffusion gradients. The one or more processors may cause, based on the one or more scan parameters, an imaging device to perform a plurality of scans to one or more slices of an object by applying the plurality of diffusion gradients to the one or more slices. For two components in a specific direction of the plurality of diffusion gradients applied in any two successive scans of the plurality of scans, there may be at most one component exceeding a first threshold. The specific direction may be one of a readout direction, a phase-encoding direction, or a slice-selection direction. The first threshold may be less than diffusion gradient energy relating to a duration and strength associated with one of the plurality of diffusion gradients.

In some embodiments, if a component in the specific direction of a first diffusion gradient applied in a first scan exceeds the first threshold, a component in the specific direction of a second diffusion gradient applied in a second scan may be below a second threshold, the second scan being performed next to the first scan, the first threshold being greater than the second threshold.

In some embodiments, to cause, based on the one or more scan parameters, the imaging device to perform the plurality of scans to the one or more slices of the object, the one or more processors may determine a list by arranging the plurality of diffusion gradients such that if a component in the specific direction of a first diffusion gradient applied in a first scan exceeds the first threshold, a component in the specific direction of a second diffusion gradient applied in a second scan is below a second threshold that is less than the first threshold, the second scan being performed next to the first scan. The one or more processors may cause the imaging device to perform the plurality of scans by applying the plurality of diffusion gradients to the one or more slices based on the list.

In some embodiments, the first threshold may be in a range of 70%-90% of the diffusion gradient energy, and the second threshold may be in a range of 30%-50% of the diffusion gradient energy.

In some embodiments, the specific direction may be the readout direction.

In some embodiments, to cause, based on the one or more scan parameters, the imaging device to perform the plurality of scans to the one or more slices of the object, the one or more processors may cause, based on the one or more scan parameters, the imaging device to perform a third scan of the plurality of scans by applying a third diffusion gradient of the plurality of diffusion gradients to a third slice of the one or more slices of the object. The one or more processors may cause, based on the one or more scan parameters, the imaging device to perform, immediately after the third scan, a fourth scan of the plurality of scans by applying a fourth diffusion gradient of the plurality of diffusion gradients to a fourth slice of the one or more slices of the object. The third slice may be different from the fourth slice.

In some embodiments, the fourth slice may be next to the third slice.

In some embodiments, to cause, based on the one or more scan parameters, the imaging device to perform the plurality of scans to the one or more slices of the object, the one or more processors may cause, based on the one or more scan parameters, the imaging device to perform a third scan of the plurality of scans by applying a third diffusion gradient of the plurality of diffusion gradients to a third slice of the one or more slices of the object. The one or more processors may cause, based on the one or more scan parameters, the imaging device to perform, immediately after the third scan, a fourth scan of the plurality of scans by applying a fourth diffusion gradient of the plurality of diffusion gradients to the third slice.

In some embodiments, the one or more processors may obtain imaging data related to the one or more slices based on the plurality of scans. The one or more processors may generate one or more images based on the imaging data.

According to another aspect of the present disclosure, a method for MRI may include one or more of the following operations. One or more processors may obtain one or more scan parameters. The one or more scan parameters may include information of a plurality of diffusion gradients. The one or more processors may cause, based on the one or more scan parameters, an imaging device to perform a plurality of scans to one or more slices of an object by applying the plurality of diffusion gradients to the one or more slices. For two components in a specific direction of the plurality of diffusion gradients applied in any two successive scans of the plurality of scans, there may be at most one component exceeding a first threshold. The specific direction may be one of a readout direction, a phase-encoding direction, or a slice-selection direction. The first threshold may be less than diffusion gradient energy relating to a duration and strength associated with one of the plurality of diffusion gradients.

According to yet another aspect of the present disclosure, a system for MRI may include a parameter obtaining module configured to obtain one or more scan parameters. The one or more scan parameters may include information of a plurality of diffusion gradients. The system may include a control module configured to cause, based on the one or more scan parameters, an imaging device to perform a plurality of scans to one or more slices of an object by applying the plurality of diffusion gradients to the one or more slices. For two components in a specific direction of the plurality of diffusion gradients applied in any two successive scans of the plurality of scans, there may be at most one component exceeding a first threshold. The specific direction may be one of a readout direction, a phase-encoding direction, or a slice-selection direction. The first threshold may be less than diffusion gradient energy relating to a duration and strength associated with one of the plurality of diffusion gradients.

According to yet another aspect of the present disclosure, a non-transitory computer readable medium may comprise at least one set of instructions. The at least one set of instructions may be executed by one or more processors of a computer server. The one or more processors may obtain one or more scan parameters. The one or more scan parameters may include information of a plurality of diffusion gradients. The one or more processors may cause, based on the one or more scan parameters, an imaging device to perform a plurality of scans to one or more slices of an object by applying the plurality of diffusion gradients to the one or more slices. For two components in a specific direction of the plurality of diffusion gradients applied in any two successive scans of the plurality of scans, there may be at most one component exceeding a first threshold. The specific direction may be one of a readout direction, a phase-encoding direction, or a slice-selection direction. The first threshold may be less than diffusion gradient energy relating to a duration and strength associated with one of the plurality of diffusion gradients.

According to yet another aspect of the present disclosure, a system for MRI may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain one or more scan parameters. The one or more scan parameters includes information of a plurality of diffusion gradients. The one or more processors may cause, based on the one or more scan parameters, the imaging device to perform a plurality of scans by applying the plurality of diffusion gradients to one or more slices of the object. Scan directions of two successive scans of the plurality of scans may be different.

According to yet another aspect of the present disclosure, a method for MRI may include one or more of the following operations. One or more processors may obtain one or more scan parameters. The one or more scan parameters includes information of a plurality of diffusion gradients. The one or more processors may cause, based on the one or more scan parameters, the imaging device to perform a plurality of scans by applying the plurality of diffusion gradients to one or more slices of the object. Scan directions of two successive scans of the plurality of scans may be different.

According to yet another aspect of the present disclosure, a system for MRI may include an parameter obtaining module configured to obtain one or more scan parameters. The one or more scan parameters may include information of a plurality of diffusion gradients. The system may include a control module configured to cause, based on the one or more scan parameters, the imaging device to perform a plurality of scans by applying the plurality of diffusion gradients to one or more slices of the object. Scan directions of two successive scans of the plurality of scans may be different.

According to yet another aspect of the present disclosure, a non-transitory computer readable medium may comprise at least one set of instructions. The at least one set of instructions may be executed by one or more processors of a computer server. The one or more processors may obtain one or more scan parameters. The one or more scan parameters includes information of a plurality of diffusion gradients. The one or more processors may cause, based on the one or more scan parameters, the imaging device to perform a plurality of scans by applying the plurality of diffusion gradients to one or more slices of the object. Scan directions of two successive scans of the plurality of scans may be different.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 7A is a flowchart illustrating an exemplary process for diffusion tensor imaging (DTI) according to some embodiments of the present disclosure;

FIG. 8 is a flowchart illustrating an exemplary process for arranging a plurality of diffusion gradients according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 3:
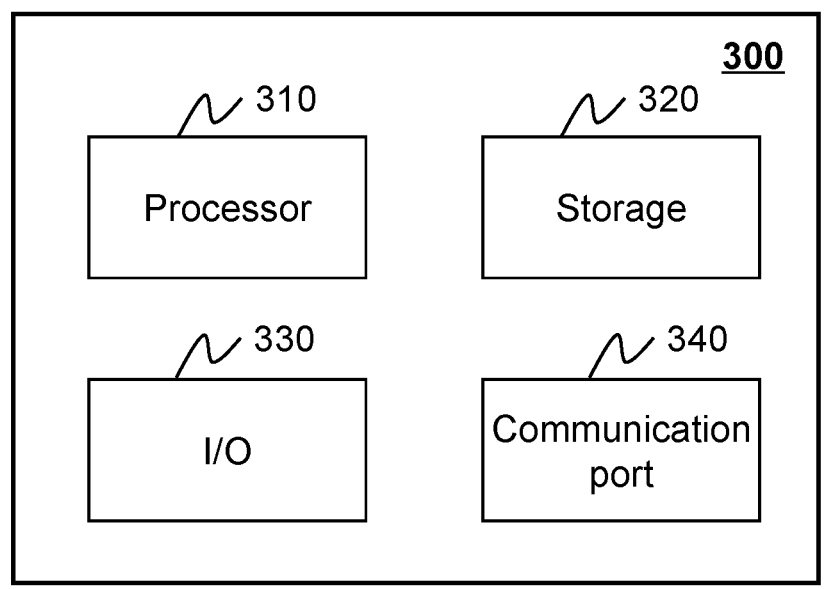
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system. Exemplary MRI systems may include a superconducting magnetic resonance imaging system, a non-superconducting magnetic resonance imaging system, etc. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), image-guide radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

An aspect of the present disclosure relates to systems and methods for DTI. For each of a plurality of scans, the systems and/or methods may determine which of a plurality of diffusion gradients is to be applied in the scan, so that the MRI scanner may scan one or more slices of an object by applying, in a certain scan order, the plurality of diffusion gradients. According to the scan order, for two components in a specific direction of two of the plurality of diffusion gradients applied in any two successive scans of the plurality of scans, there may be at most one component exceeding a first threshold. According to the scan order, if a component in the specific direction of a first diffusion gradient applied in a first scan exceeds the first threshold, the component in the specific direction of a second diffusion gradient applied in a second scan may be below a second threshold. The second scan may be performed next to the first scan. The first threshold may be greater than the second threshold.

In this way, the condition that the gradient amplifier in a specific direction (e.g., the readout direction, the phase-encoding direction, or the slice-selection direction) works at a high power successively may be avoided and the stability of the gradient amplifiers may be improved.

For brevity, the description of the methods and/or systems for MRI in the present disclosure may take DTI as an example. It should be noted that the methods and/or systems for DTI is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the methods and/or systems for MRI described in the present disclosure may also be applied to other diffusion imaging, such as echo planar imaging-diffusion tensor imaging (EPI-DTI), fast spin echo-diffusion tensor imaging (FSE-DTI), echo planar imaging-diffusion weighted imaging (EPI-DWI), fast spin echo-diffusion weighted imaging (FSE-DWI), or the like. As another example, the methods and/or systems for MRI described in the present disclosure may also be applied to flow compensation (FC).

Figure 1:
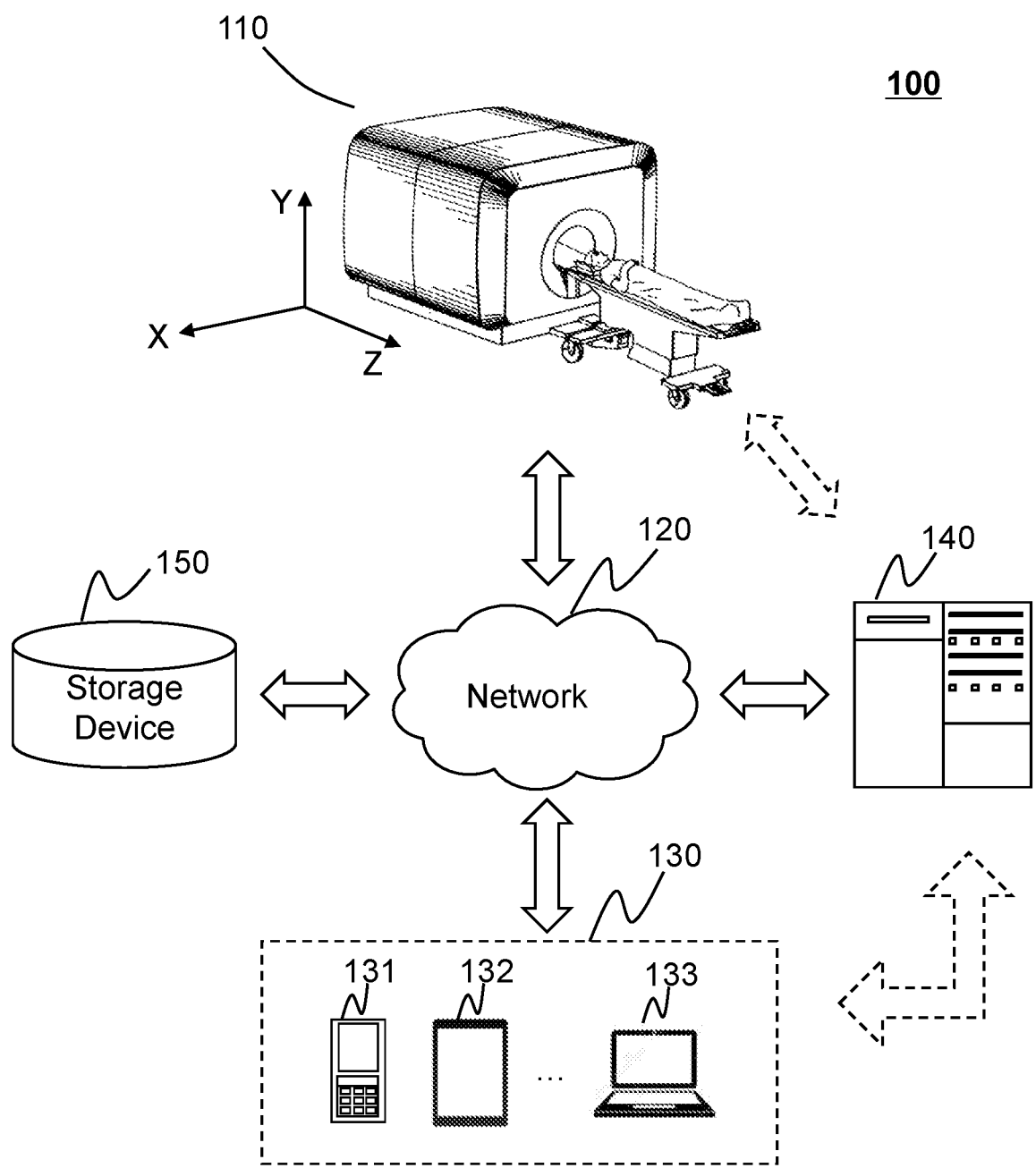
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As illustrated, the MRI system 100 may include an MRI scanner 110, a network 120, a terminal 130, a processing device 140, and a storage device 150. The components of the MRI system 100 may be connected in one or more of various ways. Mere by way of example, as illustrated in FIG. 1, the MRI scanner 110 may be connected to the processing device 140 through the network 120. As another example, the MRI scanner 110 may be connected to the processing device 140 directly (as indicated by the bi-directional arrow in dotted lines linking the MRI scanner 110 and the processing device 140). As a further example, the storage device 150 may be connected to the processing device 140 directly or through the network 120. As still a further example, a terminal device (e.g., 131, 132, 133, etc.) may be connected to the processing device 140 directly (as indicated by the bi-directional arrow in dotted lines linking the terminal 130 and the processing device 140) or through the network 120.

The MRI scanner 110 may scan an object located within its detection region and generate a plurality of data relating to the object. In the present disclosure, "subject" and "object" are used interchangeably. Mere by way of example, the object may include a patient, a man-made object, etc. As another example, the object may include a specific portion, organ, and/or tissue of a patient. For example, the object may include the head, the brain, the neck, the body, a shoulder, an arm, the thorax, the heart, the stomach, a blood vessel, soft tissue, a knee, feet, or the like, of a patient, or any combination thereof. In some embodiments, the MRI scanner 110 may be a close-bore scanner or an open-bore scanner. In the present disclosure, the X axis, the Y axis, and the Z axis shown in FIG. 1 may form an orthogonal coordinate system. The X axis and the Z axis shown in FIG. 1 may be horizontal, and the Y axis may be vertical. As illustrated, the positive X direction along the X axis may be from the right side to the left side of the MRI scanner 110 seen from the direction facing the front of the MRI scanner 110; the positive Y direction along the Y axis shown in FIG. 1 may be from the lower part to the upper part of the MRI scanner 110; the positive Z direction along the Z axis shown in FIG. 1 may refer to a direction in which the object is moved out of the scanning channel (or referred to as the bore) of the MRI scanner 110. More description of the MRI scanner 110 may be found elsewhere in the present disclosure. See, e.g., FIG. 2 and the description thereof.

The network 120 may include any suitable network that can facilitate the exchange of information and/or data for the MRI system 100. In some embodiments, one or more components of the MRI system 100 (e.g., the MRI scanner 110, the terminal 130, the processing device 140, or the storage device 150) may communicate information and/or data with one or more other components of the MRI system 100 via the network 120. For example, the processing device 140 may obtain imaging data from the MRI scanner 110 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the MRI system 100 may be connected to the network 120 to exchange data and/or information.

The terminal 130 include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the terminal 130 may remotely operate the MRI scanner 110 and/or the processing device 140. In some embodiments, the terminal 130 may operate the MRI scanner 110 and/or the processing device 140 via a wireless connection. In some embodiments, the terminal 130 may receive information and/or instructions inputted by a user, and send the received information and/or instructions to the MRI scanner 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the MRI scanner 110, the terminal 130, and/or the storage device 150. For example, the processing device 140 may obtain, from the storage device 150 or a terminal 130, operation information including, e.g., a designed time-domain waveform and correct the designed time-domain waveform. In some embodiments, the processing device 140 may be a single server, or a server group. The server group may be centralized or distributed. In some embodiments, the processing device 140 may be local or remote. For example, the processing device 140 may access information and/or data stored in or acquired by the MRI scanner 110, the terminal 130, and/or the storage device 150 via the network 120. As another example, the processing device 140 may be directly connected to the MRI scanner 110 (as illustrated by the bidirectional arrow in dashed lines connecting the processing device 140 and the MRI scanner 110 in FIG. 1), the terminal 130 (as illustrated by the bidirectional arrow in dashed lines connecting the processing device 140 and the terminal 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300 having one or more components illustrated in FIG. 3 in the present disclosure.

The storage device 150 may store data and/or instructions. In some embodiments, the storage device 150 may store data obtained from the MRI scanner 110, the terminal 130 and/or the processing device 140. For example, the storage device 150 may store a list including a plurality of diffusion gradients that are applied to one or more slices in a plurality of scans. In some embodiments, the storage device 150 may store data and/or instructions that the processing device 140 may execute or use to perform exemplary methods described in the present disclosure. For example, the storage device 150 may store instructions that the processing device 140 may execute to determine a diffusion gradient for each scan. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the MRI system 100 (e.g., the MRI scanner 110, the processing device 140, the terminal 130, etc.). One or more components of the MRI system 100 may access the data or instructions stored in the storage device 150 via the network 120. In some embodiments, the storage device 150 may be directly connected to or communicate with one or more components of the MRI system 100 (e.g., the MRI scanner 110, the processing device 140, the terminal 130, etc.). In some embodiments, the storage device 150 may be part of the processing device 140.

In some embodiments, the MRI system 100 may further include one or more power supplies (not shown in FIG. 1) connected to one or more components of the MRI system 100 (e.g., the MRI scanner 110, the processing device 140, the terminal 130, the storage device 150, etc.).

Figure 2:
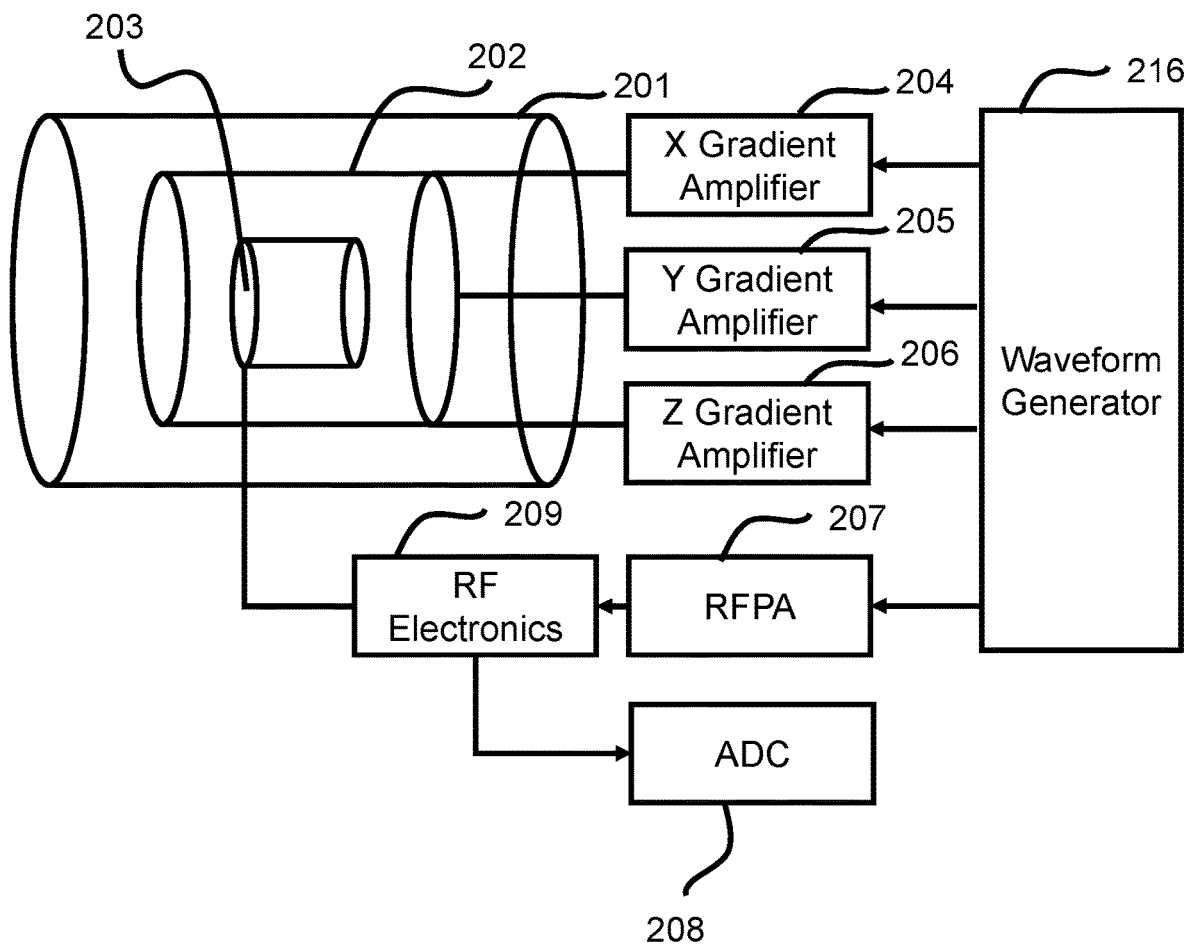
FIG. 2 is a schematic diagram illustrating an exemplary MRI scanner according to some embodiments of the present disclosure.

FIG. 2 is a schematic diagram illustrating an exemplary MRI scanner according to some embodiments of the present disclosure. As illustrated, the main magnet 201 may generate a first magnetic field (or referred to as a main magnetic field) that may be applied to an object (also referred to as a subject) exposed inside the field. The main magnet 201 may include a resistive magnet or a superconductive magnet that both need a power supply (not shown) for operation. Alternatively, the main magnet 201 may include a permanent magnet. The main magnet 201 may include a bore that the object is placed within. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of an object may vary as a function of their positions inside the gradient field, thereby encoding spatial information into MR signals generated by the region of the object being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of MR signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis (e.g., a readout direction), the Y-axis (e.g., a phase-encoding direction), or the Z-axis (e.g., a slice-selection direction), respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate MR signals related to the region of the object being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting MR signals (e.g., echoes). After excitation, the MR signals generated by the object may be sensed by the RF coils 203. The receiver amplifier may then receive the sensed MR signals from the RF coils 203, amplify the sensed MR signals, and provide the amplified MR signals to the ADC 208. The ADC 208 may transform the MR signals from analog signals to digital signals. The digital MR signals may then be sent to the processing device 140 for sampling.

In some embodiments, the gradient coils 202 and the RF coils 203 may be circumferentially positioned with respect to the object. It is understood by those skilled in the art that the main magnet 201, the gradient coils 202, and the RF coils 203 may be situated in a variety of configurations around the object.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the MRI scanner 110 may further include an object positioning system (not shown). The object positioning system may include an object cradle and a transport device. The object may be placed on the object cradle and be positioned by the transport device within the bore of the main magnet 201.

MRI systems (e.g., the MRI system 100 in the present disclosure) may be commonly used to obtain an image of an interior region of interest of a patient that can be used for the purposes of, e.g., diagnosis, treatment, or the like, or a combination thereof. MRI systems include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an MR signal. The MR signal may be detected and processed to form an MR image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient, magnetic field gradients Gx, Gy, and Gz (e.g., generated by the gradient coils 202) in the x, y, and z directions, having a particular timing, frequency, and phase, may be superimposed on the uniform magnetic field such that the RF excitation signal excites the H atoms in a desired slice of the patient's body, and unique phase and frequency information is encoded in the MR signal depending on the location of the H atoms in the "image slice."

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number (or count) of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include fast spin echo (FSE), turbo spin echo (TSE), rapid acquisition with relaxation enhancement (RARE), half-Fourier acquisition single-shot turbo spin-echo (HASTE), turbo gradient spin echo (TGSE), or the like, or any combination thereof. The protocol may also include information regarding image contrast and/or ratio, an ROI, slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number (or count) of phases, the number (or count) of excitations (NEX), inversion time, bandwidth (e.g., RF receiver bandwidth, RF transmitter bandwidth, etc.), or the like, or any combination thereof.

For each MRI scan, the resulting MR signals may be digitized and processed to reconstruct an image in accordance with the MRI imaging protocol that is used.

FIG. 3 is a schematic diagram illustrating exemplary hardware and/or software components of a computing device on which the processing device 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 310 may obtain, from the storage device 150 and/or a terminal 130, a list including a plurality of diffusion gradients that are applied to one or more slices in a plurality of scans. In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be noted that the computing device 300 in the present disclosure may also include multiple processors, and thus operations of a method that are performed by one processor as described in the present disclosure may also be jointly or separately performed by the multiple processors. For example, if in the present disclosure the processor of the computing device 300 executes both operations A and B, it should be understood that operations A and step B may also be performed by two different processors jointly or separately in the computing device 300 (e.g., a first processor executes operation A and a second processor executes operation B, or the first and second processors jointly execute operations A and B).

Merely by way example, the processor 310 may receive instructions to follow an MRI scan protocol for imaging/scanning the object. For example, the processor 310 may instruct the object positioning system of the MRI scanner 110 to move the object to a proper position within the bore of the main magnet 201. As another example, the processor 310 may also provide certain control signals to control the main magnet 201 to generate a main magnet field with a specific strength.

The processor 310 may receive control signals to set the shape, amplitude, and/or timing of the gradient waveforms and/or the RF waveforms, and send the set parameters to the waveform generator 216 to instruct the waveform generator 216 to generate a particular gradient waveform sequence and pulse sequence that are to be applied to the gradient coils 202 and the RF coils 203 through the amplifiers 204-207, respectively.

The processor 310 may also sample data (e.g., echoes) from the RF coils 203 based on one or more sampling parameters including, e.g., timing information (e.g., the length of data acquisition), the type of k-space data acquisition (e.g., undersampling, oversampling, etc.), sampling trajectory (e.g., Cartesian trajectory, non-Cartesian trajectory such as spiral trajectory, radial trajectory), or the like, or a combination thereof. In some embodiments, the timing information may be input by a user (e.g., an operator) or autonomously determined by the MRI system 100 based on one or more other parameters (e.g., clinical needs) of an imaging process. The timing information may correspond to the type of the gradient and RF waveforms that are sent to the gradient coils 202 and the RF coils 203, respectively, so that the MR signals are correctly sampled. The processor 310 may also generate an MR image by reconstructing the sampled data.

The storage 320 may store data/information obtained from the MRI scanner 110, the terminal 130, the storage device 150, or any other component of the MRI system 100. In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 140 for determining a diffusion gradient for each scan.

The I/O 330 may input or output signals, data, or information. In some embodiments, the I/O 330 may enable user interaction with the processing device 140. In some embodiments, the I/O 330 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

Merely by way of example, a user (e.g., an operator) of the processing device 140 may input data related to an object (e.g., a patient) that is being/to be imaged/scanned through the I/O 330. The data related to the object may include identification information (e.g., the name, age, gender, medical history, contract information, physical examination result, etc.) and/or the test information including the nature of the MRI scan that needs to be performed. The user may also input parameters needed for the operation of the MRI scanner 110, such as image contrast and/or ratio, a region of interest (ROI), slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with steady-state procession, and so on), a flip angle value, acquisition time (TA), echo time (TE), repetition time (TR), echo train length (ETL), the number (or count) of phases, the number (or count) of excitations (NEX), inversion time, bandwidth (e.g., RF receiver bandwidth, RF transmitter bandwidth, etc.), a scan type, a type of sampling, or the like, or any combination thereof. The I/O may also display MR images generated based on the sampled data.

The communication port 340 may be connected to a network (e.g., the network 120) to facilitate data communications. The communication port 340 may establish connections between the processing device 140 and the MRI scanner 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
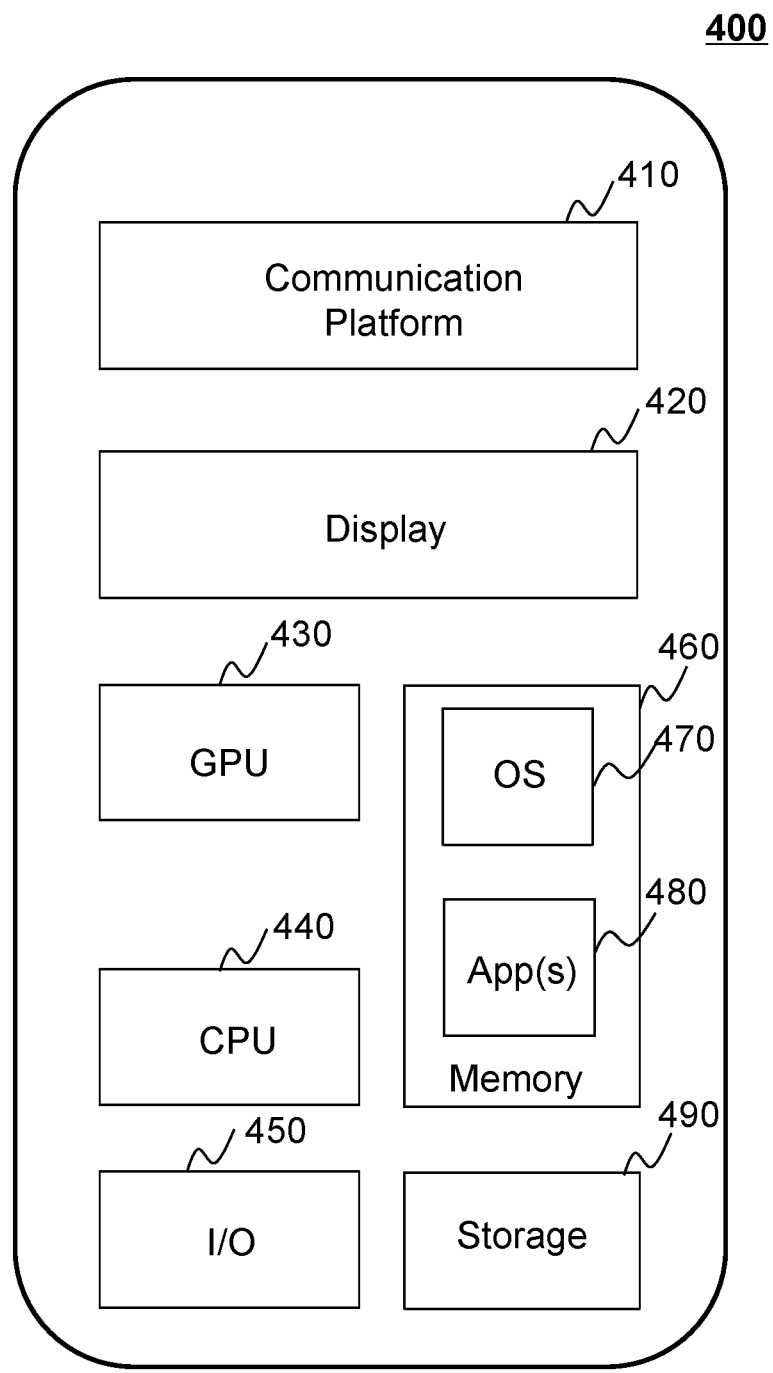
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which the terminal 130 may be implemented according to some embodiments of the present disclosure. As illustrated in FIG. 4, the mobile device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the MRI system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5:
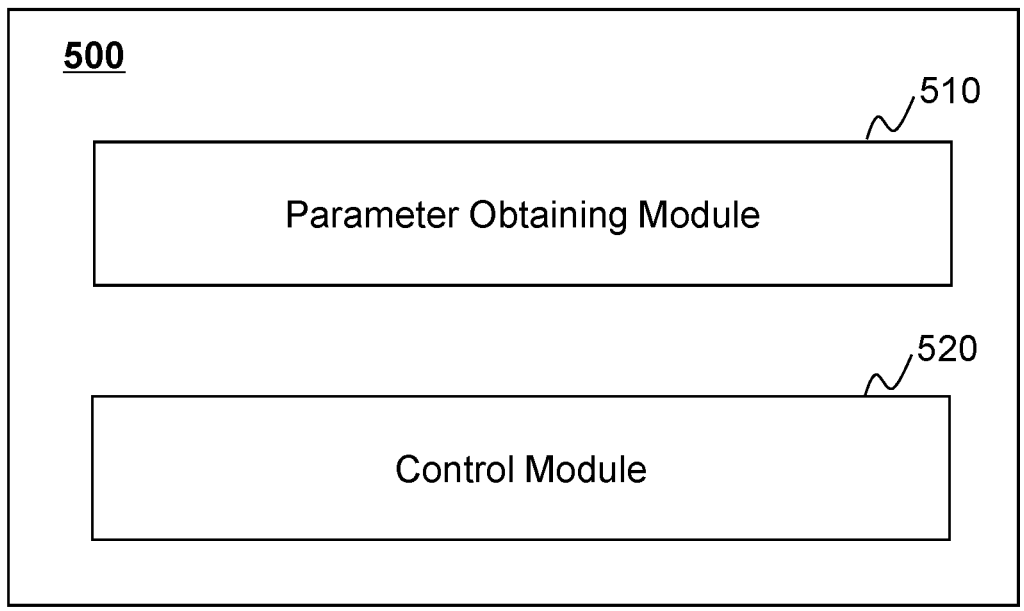
FIG. 5 is a schematic block diagram illustrating an exemplary processing device according to some embodiments of the present disclosure.

FIG. 5 is a schematic block diagram illustrating an exemplary processing device according to some embodiments of the present disclosure. The processing device 140 may include a parameter obtaining module 510 and a control module 520.

The parameter obtaining module 510 may obtain one or more scan parameters. In some embodiments, the one or more scan parameters may include information regarding image contrast and/or ratio, an ROI, slice thickness, the number (or count) of slices, the number (or count) of scans, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number (or count) of phases, the number (or count) of excitations (NEX), inversion time, bandwidth (e.g., RF receiver bandwidth, RF transmitter bandwidth, etc.), information (e.g., the strength, waveform, duration, frequency, starting time, etc.) of the RF pulse, the slice-selection gradient, the readout gradient, and the phase-encoding gradient, or the like, or any combination thereof. In some embodiments, the one or more scan parameters may further include information of the plurality of diffusion gradients, such as the waveform, starting time, duration, frequency, strength, direction, components in three different directions (e.g., the slice-selection direction, the readout direction, and the phase-encoding direction), the number (or count) of the plurality of the diffusion gradients, or the like, or any combination thereof.

In some embodiments, the strength, duration, and waveform of each of the plurality of diffusion gradients may be the same, and the directions of the plurality of diffusion gradients may be different.

In some embodiments, the parameter obtaining module 510 may obtain the one or more scan parameters from a storage medium (e.g., the storage device 150 and/or the storage 320) of the MRI system 100, from a user, etc.

The control module 520 may cause, based on the one or more scan parameters, an imaging device (e.g., the MRI scanner 110) to perform a plurality of scans by applying the plurality of diffusion gradients to the one or more slices of an object.

In some embodiments, for each of the plurality of scans, the control module 520 may determine which of the plurality of diffusion gradients is to be applied in the scan, so that the control module 520 may cause the MRI scanner 110 to scan the one or more slices by applying, in a certain scan order, the plurality of diffusion gradients, which may avoid or mitigate the condition that the gradient amplifier in a specific direction (e.g., the X gradient amplifier 204, the Y gradient amplifier 205, or the Z gradient amplifier 206) continuously works at a high power for an extended period of time and improve the stability of one or more of the gradient amplifiers, e.g., the X gradient amplifier 204, the Y gradient amplifier 205, and the Z gradient amplifier 206.

In some embodiments, according to the scan order, for two components in a specific direction of two of the plurality of diffusion gradients applied in any two successive scans of the plurality of scans, there may be at most one component exceeding a first threshold. The specific direction may be one of the readout direction, the phase-encoding direction, or the slice-selection direction. The first threshold may be less than diffusion gradient energy. The diffusion gradient energy may relate to a duration and strength associated with one of the plurality of diffusion gradients.

In some embodiments, the first threshold may be in a range of 70%-90% of the diffusion gradient energy.

In some embodiments, according to the scan order, if a component in the specific direction of a first diffusion gradient applied in a first scan exceeds the first threshold, the component in the same specific direction of a second diffusion gradient applied in a second scan may be below a second threshold. The second scan may be performed next to the first scan. The first threshold may be greater than the second threshold. For instance, the first threshold may be in a range of 70%-90% of the diffusion gradient energy, while the second threshold may be in a range of 30%-50% of the diffusion gradient energy.

In some embodiments, the control module 520 may cause, based on the one or more scan parameters, the MRI scanner 110 to perform two successive scans to two different slices, such as two neighboring slices.

In some embodiments, the control module 520 may cause, based on the one or more scan parameters, the MRI scanner 110 to perform two successive scans to the same slice.

In some embodiments, when determining which diffusion gradient is applied to each scan, the control module 520 may consider the characteristic of at least one of the X gradient amplifier 204, the Y gradient amplifier 205, and the Z gradient amplifier 206, such as the root mean square (RMS) power, gradient instantaneous power, coil temperature, etc. Merely by way of example, the processing device 140 may consider only the characteristic of the gradient amplifier in the readout direction (e.g., the X gradient amplifier 204).

For example, for different arrangement results of the plurality of diffusion gradients, the control module 520 may estimate the RMS power, the gradient instantaneous power, and the coil temperature of at least one of the X gradient amplifier 204, the Y gradient amplifier 205, and the Z gradient amplifier 206. The processing device 140 may select a arrangement result corresponding to which the average value or the weighted average value of the RMS power, the gradient instantaneous power, and the coil temperature is minimum.

In some embodiments, the processing device 140 may further include an image generation module configured to obtain imaging data related to the one or more slices based on the plurality of scans and generate a plurality of images based on the imaging data.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the control module 520 may be divided into two units. One of the two unit may be configured to determine a diffusion gradient for each scan, and the other one of the two unit may be configured to cause the MRI scanner 110 to perform scans to an object.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of in the processing device 140. As another example, each of the components of the processing device 140 may include a storage device. Additionally or alternatively, the components of the processing device 140 may share a common storage device.

Diffusion-weighted magnetic resonance imaging (DWI or DW-MRI) is an imaging process that uses molecular diffusion, e.g., the diffusion of water molecules, to generate contrast in magnetic resonance (MR) images. DWI may allow the mapping of the diffusion process of molecules, e.g., water, in biological tissue, in vivo and non-invasively. Molecular diffusion in tissue is not free, but may reflect interactions with many obstacles, such as macromolecules, fibers, and membranes. Water molecule diffusion may therefore reveal microscopic details about tissue architecture, either normal or in a diseased state.

MRI may be configured to be sensitive to the motion of molecules. To sensitize MRI images to diffusion, instead of a homogeneous magnetic field, the magnetic field may be varied linearly by a pulsed field gradient (also referred to as a diffusion gradient). For example, in a spin echo sequence, the diffusion gradient may be applied before the refocusing RF pulse (e.g., a 180°-pulse). Since precession is proportional to the magnet strength, the protons begin to process at different rates, resulting in dispersion of the phase and signal loss. Another gradient pulse may be applied in the same magnitude but with opposite direction to refocus or rephrase the spins. For example, in the spin echo sequence, this gradient pulse may be applied after the refocusing RF pulse (e.g., the 180°-pulse). The refocusing may be imperfect for protons that have moved during the time interval between the pulses, and the acquired MR signals may be reduced or attenuated. When water is in an environment where it can freely tumble, relaxation may tend to take longer, which may generate contrast between an area of pathology and the surrounding healthy tissue.

A special kind of DWI, diffusion tensor imaging (DTI), has been used extensively in clinical neurology, such as brain pathologies. The physical process of diffusion may cause water molecules to move out from a central point, and gradually reach the surface of an ellipsoid if the medium is anisotropic (or the surface of a sphere for an isotropic medium). The signal attenuation (caused by the effect of the diffusion gradient) of an MRI voxel may be converted into a numerical measure of diffusion—the diffusion tensor, from which a tissue diffusion profile (e.g., the diffusion anisotropy and/or the ellipsoid model of the diffusion of water molecules) may be measured.

In tissue, diffusion may lead to movement of water molecules along multiple directions. If there is an internal anisotropic organization of the tissue that constrains diffusion, then this fact may be reflected in the pattern of diffusion. The relationship between the properties of driving force that generate diffusion of the water molecules and the resulting pattern of their movement in the tissue may be described by the diffusion tensor. Merely by way of example, the collection of molecular displacements of this physical property may be described with nine components— each one associated with a pair of axes xx, yy, zz, xy, yx, xz, zx, yz, zy, for example, denoted as Equation (1) below:

$$\overline{D} = \begin{vmatrix} D_{xx} & D_{xy} & D_{xz} \\ D_{yx} & D_{yy} & D_{yz} \\ D_{zx} & D_{zy} & D_{zz} \end{vmatrix}, \quad (1)$$

where $\overline{D}$ refers to the diffusion tensor; and $D_{xx}$, $D_{xy}$, $D_{xz}$, $D_{yx}$, $D_{yy}$, $D_{yz}$, $D_{zx}$, $D_{zy}$, and $D_{zz}$ refer to the nine components associated with the axes xx, xy, xz, yx, yy, yz, zx, zy, and zz, respectively. As used herein, the x, y, and z axes may be similar to the X, Y, and Z axes in FIG. 1.

Each diffusion gradient applied may measure the movement of water molecules along the direction of that diffusion gradient. In DTI, six or more non-colinear diffusion gradients may be summed to get all the measurements needed to fill in Equation (1), assuming it is symmetric above and below the diagonal of the matrix in Equation (1) that goes through $D_{xx}$, $D_{yy}$, and $D_{zz}$. The more non-colinear diffusion gradients are applied, the more accurate the estimated diffusion tensor may be.

In some embodiments, the processing device 140 may cause the MRI scanner 110 to perform a plurality of scans by applying a plurality of diffusion gradients (e.g., at least six non-colinear diffusion gradients in at least six directions, respectively) to one or more slices of an object. In some embodiments, the processing device 140 may cause the MRI scanner 110 to perform traversal scanning in the one or more slices by applying the plurality of diffusion gradients. For example, for each of the one or more slices, the processing device 140 may cause the MRI scanner 110 to perform scans by applying the plurality of diffusion gradients to the slice. One of the plurality of diffusion gradients may be applied to the slice in one scan.

For example, if a user (e.g., a doctor, a technician, or an engineer) of the MRI system 100 defines 3 slices of an object and 64 diffusion gradients that are in 64 different directions, for each of the 3 slices, the processing device 140 may cause the MRI scanner 110 to perform 64 scans by applying the 64 diffusion gradients to the slice in the 64 scans, respectively, thereby leading to 192 scans in the whole process.

In some embodiments, during a scan by applying one of the plurality of diffusion gradients to a slice, the waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the readout direction, the slice-selection direction, and the phase-encoding direction, respectively, which are components of the diffusion gradient in the readout direction, the slice-selection direction, and the phase-encoding direction, respectively, and form the diffusion gradient. As used in the present disclosure, the component in the readout direction of a diffusion gradient may be referred to as a first component of the diffusion gradient, the component in the phase-encoding direction of a diffusion gradient may be referred to as a second component of the diffusion gradient, and the component in the slice-selection direction of a diffusion gradient may be referred to as a third component of the diffusion gradient.

In some embodiments, in order to obtain more information to estimate the diffusion tensor, diffusion gradients in more (e.g., 64 or 128) directions may be applied to each of the one or more slices, which brings higher workload of the X gradient amplifier 204, the Y gradient amplifier 205, and/or the Z gradient amplifier 206. Merely by way of example, to perform EPI-DTI, during the scanning process, the polarity of the applied frequency-encoding gradients (also referred to as readout gradients) may be switched continuously. Echoes may be collected with each switch of the polarity of the readout gradients. In this case, the workload of the gradient amplifier for the readout gradient (e.g., the X gradient amplifier 204) may be high. Therefore, it is important to improve the stability of the X gradient amplifier 204, the Y gradient amplifier 205, and the Z gradient amplifier 206, especially the X gradient amplifier 204.

Traditionally, the processing device 140 may cause the MRI scanner 110 to perform the plurality of scans to the one or more slices in the following order. The processing device 140 may cause the MRI scanner 110 to successively scan the one or more slices by applying a diffusion gradient to each of the one or more slices, then cause the MRI scanner 110 to successively scan the one or more slices by applying another diffusion gradient to each of the one or more slices, and the like. In this way, if a component in a specific direction (e.g., the readout direction, the slice-selection direction, or the phase-encoding direction) of a diffusion gradient is relatively large (e.g., the direction of the diffusion gradient is almost parallel to the readout direction, the slice-selection direction, or the phase-encoding direction), and there are relatively more slices, the gradient amplifier in the specific direction may work at a high power successively, which may damage the performance of the gradient amplifier, reduce the life of the gradient amplifier, and even make the gradient amplifier overheat, fume, deform, and/or burn, thereby reducing the efficiency of the DTI.

Figure 6:
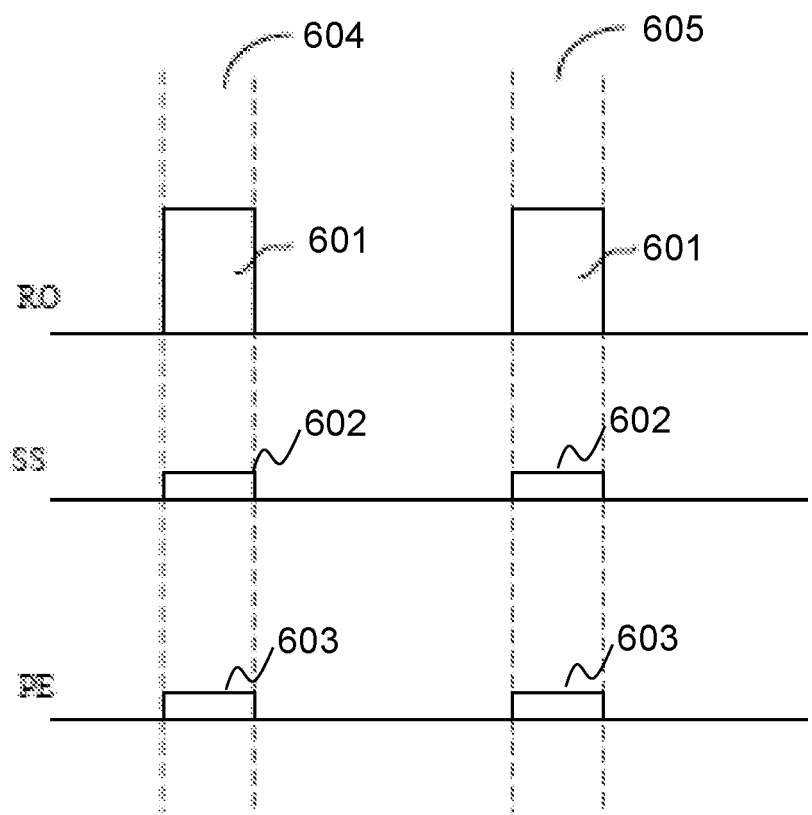
FIG. 6 is a schematic diagram illustrating an exemplary pulse sequence of traditional DTI.

Merely by way of example, as shown in FIG. 6, components 601-603 are components in the readout (abbreviated as RO in FIG. 6) direction, the slice-selection (abbreviated as SS in FIG. 6) direction, and the phase-encoding (abbreviated as PE in FIG. 6) direction of a diffusion gradient, respectively. As shown in FIG. 6, the components 602 and 603 of the diffusion gradient are relatively small. The component 601 in the readout direction of the diffusion gradient, however, is relatively large. If the processing device 140 causes the MRI scanner 110 to successively perform scans 604 and 605 by applying the diffusion gradient to two slices, the amplifier in the readout direction (e.g., the X gradient amplifier 204) may continuously work at a high power.

Alternatively, the processing device 140 may cause the MRI scanner 110 to perform the plurality of scans to the one or more slices in the following order. The processing device 140 may cause the MRI scanner 110 to perform scans to a slice by successively applying the plurality of diffusion gradients to the slice, then cause the MRI scanner 110 to perform scans to another slice by successively applying the plurality of diffusion gradients, and the like. In this way, the condition that the gradient amplifier in the specific direction may continuously work at a high power may also occur.

If the strength of the diffusion gradients is reduced and/or the duration of the diffusion gradients is extended to decrease the workload of the X gradient amplifier 204, the Y gradient amplifier 205, and/or the Z gradient amplifier 206, the image quality may be reduced and the scan time may be extended, which may reduce the efficiency of the DTI. However, to improve the performance of the gradient amplifier by improving the hardware may increase the cost of the DTI.

In the systems and/or methods for DTI provided in embodiments of the present disclosure, for each of the plurality of scans, the processing device 140 may determine which of the plurality of diffusion gradients is to be applied in the scan, so that the processing device 140 may cause the MRI scanner 110 to scan the one or more slices by applying, in a certain order, the plurality of diffusion gradients, which may avoid the condition that the gradient amplifier in a specific direction (e.g., the X gradient amplifier 204, the Y gradient amplifier 205, or the Z gradient amplifier 206) works at a high power successively and ensure the stability of the X gradient amplifier 204, the Y gradient amplifier 205, and the Z gradient amplifier 206.

FIG. 7A is a flowchart illustrating an exemplary process for diffusion tensor imaging (DTI) according to some embodiments of the present disclosure. In some embodiments, the process 700 may be implemented in the MRI system 100 illustrated in FIG. 1. For example, the process 700 may be stored in a storage medium (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 700 presented below are intended to be illustrative. In some embodiments, the process 700 may be accomplished with one or more additional operations not described, and/or without one or more of the operations discussed. Additionally, the order in which the operations of the process 700 as illustrated in FIG. 7A and described below is not intended to be limiting.

In 710, the processing device 140 (e.g., the parameter obtaining module 510) may obtain one or more scan parameters. In some embodiments, the one or more scan parameters may include information regarding image contrast and/or ratio, an ROI, slice thickness, the number (or count) of slices, the number (or count) of scans, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number (or count) of phases, the number (or count) of excitations (NEX), inversion time, bandwidth (e.g., RF receiver bandwidth, RF transmitter bandwidth, etc.), information (e.g., the strength, waveform, duration, frequency, starting time, etc.) of the RF pulse, the slice-selection gradient, the readout gradient, and the phase-encoding gradient, or the like, or any combination thereof. In some embodiments, the one or more scan parameters may further include information of the plurality of diffusion gradients, such as the waveform, starting time, duration, frequency, strength, direction, components in three different directions (e.g., the slice-selection direction, the readout direction, and the phase-encoding direction), the number (or count) of the plurality of the diffusion gradients, or the like, or any combination thereof.

In some embodiments, the strength, duration, and waveform of each of the plurality of diffusion gradients may be the same, and the directions of the plurality of diffusion gradients may be different.

In some embodiments, the processing device 140 may obtain the one or more scan parameters from a storage medium (e.g., the storage device 150 and/or the storage 320) of the MRI system 100, from a user, etc.

In 720, the processing device 140 (e.g., the control module 520) may cause, based on the one or more scan parameters, an imaging device (e.g., the MRI scanner 110) to perform a plurality of scans by applying the plurality of diffusion gradients to the one or more slices of an object.

In some embodiments, for each of the plurality of scans, the processing device 140 may determine which of the plurality of diffusion gradients is to be applied in the scan, so that the processing device 140 may cause the MRI scanner 110 to scan the one or more slices by applying, in a certain scan order, the plurality of diffusion gradients, which may avoid or mitigate the condition that the gradient amplifier in a specific direction (e.g., the X gradient amplifier 204, the Y gradient amplifier 205, or the Z gradient amplifier 206) continuously works at a high power for an extended period of time and improve the stability of one or more of the gradient amplifiers, e.g., the X gradient amplifier 204, the Y gradient amplifier 205, and the Z gradient amplifier 206.

In some embodiments, according to the scan order, for two components in a specific direction of two of the plurality of diffusion gradients applied in any two successive scans of the plurality of scans, there may be at most one component exceeding a first threshold. The specific direction may be one of the readout direction, the phase-encoding direction, or the slice-selection direction. The first threshold may be less than diffusion gradient energy. The diffusion gradient energy may relate to a duration and strength associated with one of the plurality of diffusion gradients. For example, the diffusion gradient energy may be determined based on Equation (2) below:

$$E=G^2\delta, \qquad (2)$$

where E refers to the diffusion gradient energy; G refers to the strength of one of the plurality of diffusion gradients; and δ refers to the duration of the one of the plurality of diffusion gradients.

In some embodiments, the first threshold may be in a range of 70%-90% of the diffusion gradient energy.

In some embodiments, according to the scan order, if a component in the specific direction of a first diffusion gradient applied in a first scan exceeds the first threshold, the component in the same specific direction of a second diffusion gradient applied in a second scan may be below a second threshold. The second scan may be performed next to the first scan. The first threshold may be greater than the second threshold. For instance, the first threshold may be in a range of 70%-90% of the diffusion gradient energy, while the second threshold may be in a range of 30%-50% of the diffusion gradient energy.

Figure 7B:
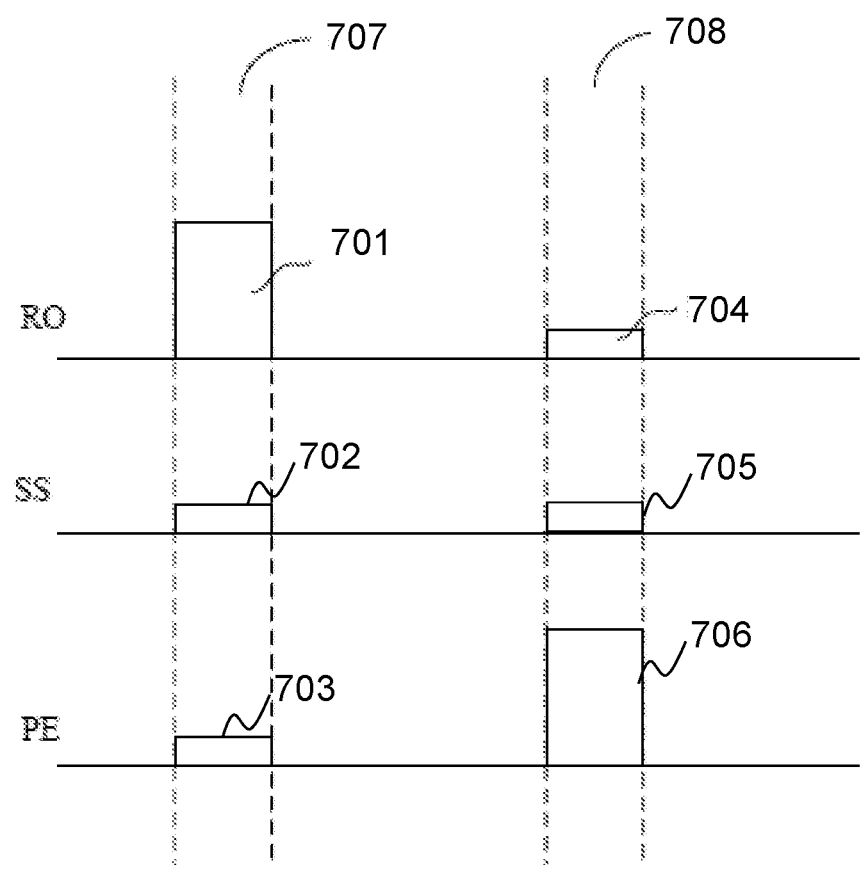
FIG. 7B is a schematic diagram illustrating an exemplary pulse sequence of DTI according to some embodiments of the present disclosure.

Merely by way of example, as shown in FIG. 7B, components 701-703 are components in the readout (abbreviated as RO in FIG. 7B) direction, the slice-selection (abbreviated as SS in FIG. 7B) direction, and the phase-encoding (abbreviated as PE in FIG. 7B) direction of diffusion gradient P, respectively, and components 704-706 are components in the readout direction, the slice-selection direction, and the phase-encoding direction of diffusion gradient Q, respectively. The component 701 in the readout direction of diffusion gradient P exceeds the first threshold. The component 708 in the readout direction of diffusion gradient Q is below the second threshold. According to the process 700, if the processing device 140 causes the MRI scanner 110 to perform scan 707 by applying diffusion gradient P, the processing device 140 may cause the MRI scanner 110 to perform, next to scan 707, scan 708 by applying diffusion gradient Q, which may relieve the workload caused by the high-power output of the amplifier in the readout direction (e.g., the X gradient amplifier 204) in scan 707.

In some embodiments, the processing device 140 may cause, based on the one or more scan parameters, the MRI scanner 110 to perform two successive scans to two different slices, such as two neighboring slices. As used herein, two slices are considered neighboring each other if there is no other slice of an object between the two slices. For example, the number (or count) of slices is 3 (e.g., slices A-C), and the number (or count) of the diffusion gradients is 64. The processing device 140 may cause the MRI scanner 110 to perform a first scan to slice A by applying a first diffusion gradient of the 64 diffusion gradients to slice A, a second scan to slice B by applying the first diffusion gradient of the 64 diffusion gradients to slice B, and a third scan to slice C by applying the first diffusion gradient of the 64 diffusion gradients to slice C. The processing device 140 may cause the MRI scanner 110 to perform a fourth scan to slice A by applying a second diffusion gradient of the 64 diffusion gradients to slice A, and the like. In addition, for each of the 192 scans, the processing device 140 may determine which of the 64 diffusion gradients is to be applied in the scan, so that the processing device 140 may cause the MRI scanner 110 to scan the 3 slices by applying, in a certain order satisfying the features of the scan order described above, the 64 diffusion gradients.

In some embodiments, the processing device 140 may cause, based on the one or more scan parameters, the MRI scanner 110 to perform two successive scans to the same slice. For example, the number (or count) of slices is 3 (e.g., slices A-C), and the number (or count) of the diffusion gradients is 64. The processing device 140 may cause the MRI scanner 110 to perform 64 scans to slice A by successively applying the 64 diffusion gradients to slice A. The processing device 140 may cause the MRI scanner 110 to perform 64 scans to slice B by successively applying the 64 diffusion gradients to slice B. The processing device 140 may cause the MRI scanner 110 to perform 64 scans to slice C by successively applying the 64 diffusion gradients to slice C. In addition, for each of the 192 scans, the processing device 140 may determine which of the 64 diffusion gradients is to be applied in the scan, so that the processing device 140 may cause the MRI scanner 110 to scan the 3 slices by applying, in a certain order satisfying the features of the scan order described above, the 64 diffusion gradients.

In some embodiments, when determining which diffusion gradient is applied to each scan, the processing device 140 may consider the characteristic of at least one of the X gradient amplifier 204, the Y gradient amplifier 205, and the Z gradient amplifier 206, such as the root mean square (RMS) power, gradient instantaneous power, coil temperature, etc. Merely by way of example, the processing device 140 may consider only the characteristic of the gradient amplifier in the readout direction (e.g., the X gradient amplifier 204).

For example, for different arrangement results of the plurality of diffusion gradients, the processing device 140 may estimate the RMS power, the gradient instantaneous power, and the coil temperature of at least one of the X gradient amplifier 204, the Y gradient amplifier 205, and the Z gradient amplifier 206. The processing device 140 may select a arrangement result corresponding to which the average value or the weighted average value of the RMS power, the gradient instantaneous power, and the coil temperature is minimum.

Figure 9:
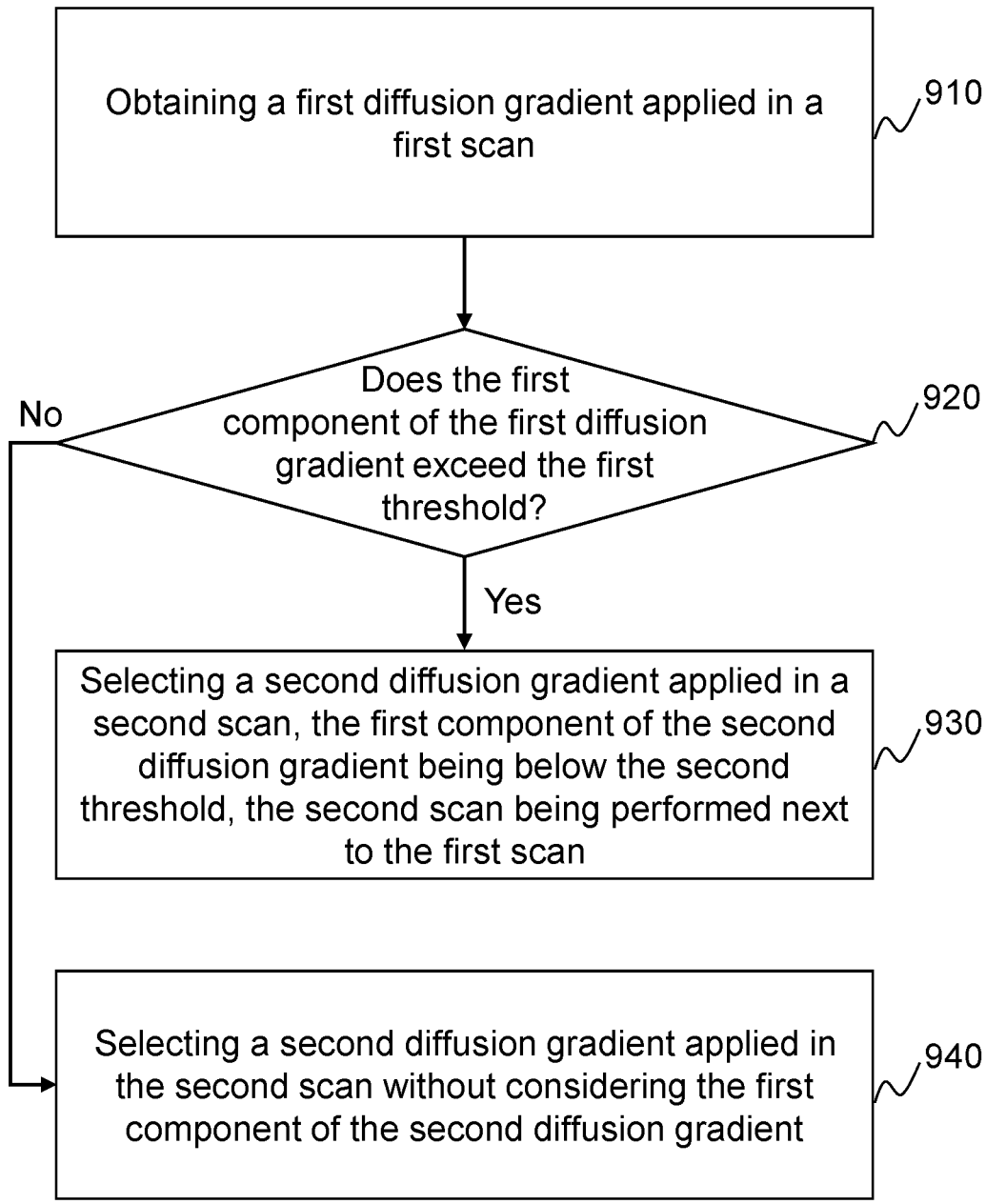
FIG. 9 is a flowchart illustrating an exemplary process for determining a diffusion gradient for a scan according to some embodiments of the present disclosure.
Figure 10:
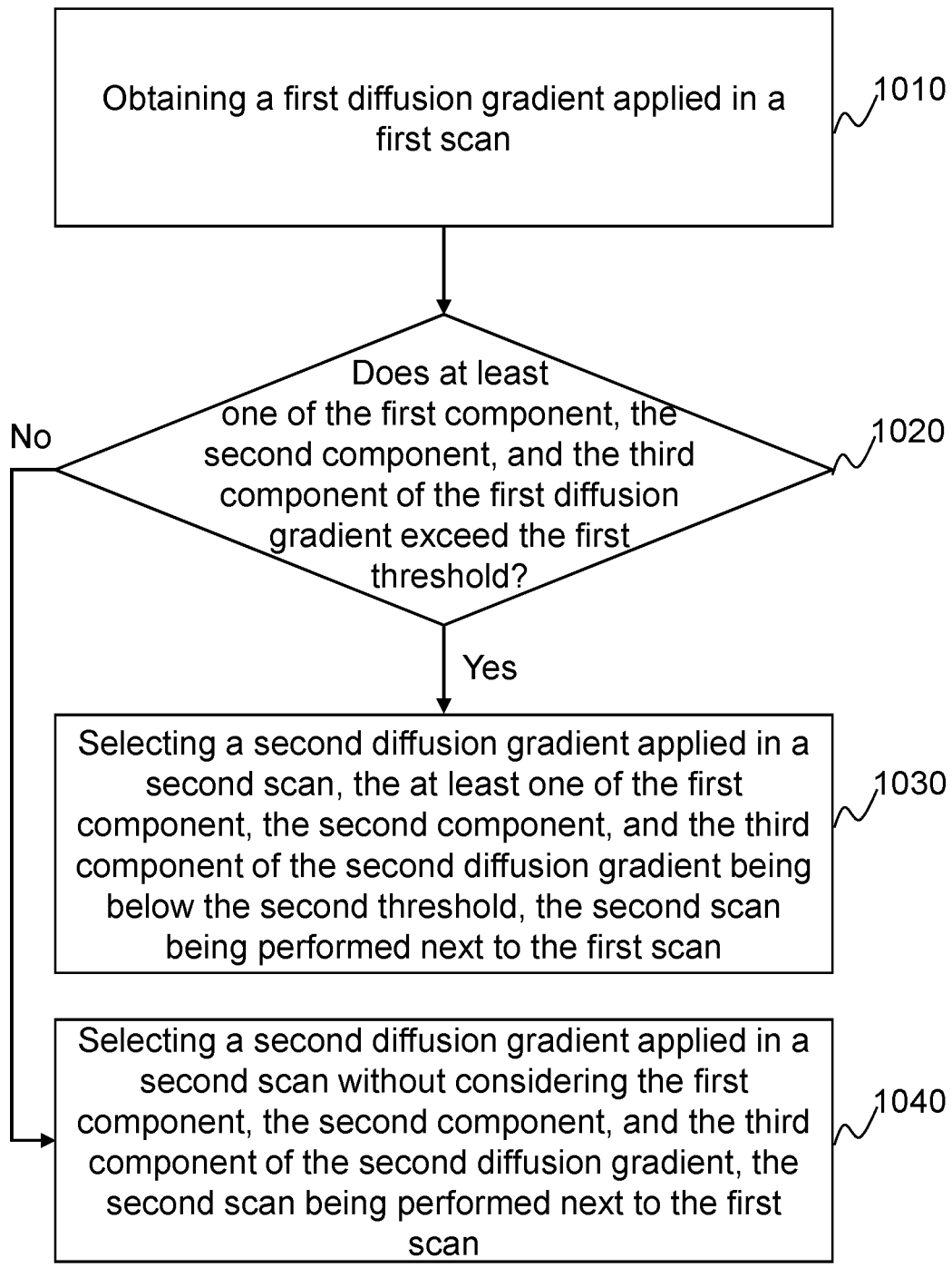
FIG. 10 is a flowchart illustrating an exemplary process for determining a diffusion gradient for a scan according to some embodiments of the present disclosure.

In some embodiments, details regarding the determination of the diffusion gradient for each scan may be found elsewhere in the present disclosure (e.g., the description in connection with FIGS. 8-10).

In some embodiments, after operation 720, the processing device 140 may further obtain imaging data related to the one or more slices based on the plurality of scans. The processing device 140 may generate a plurality of images based on the imaging data.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 8 is a flowchart illustrating an exemplary process for arranging a plurality of diffusion gradients according to some embodiments of the present disclosure. In some embodiments, the process 800 may be implemented in the MRI system 100 illustrated in FIG. 1. For example, the process 800 may be stored in a storage medium (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 800 presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In some embodiments, the processing device 140 may generate, in advance, a list by arranging the plurality of diffusion gradients. The processing device 140 may cause the MRI scanner 110 to perform the plurality of scans by applying the plurality of diffusion gradients to the one or more slices based on the list.

In some embodiments, according to the list, for two components in a specific direction of two neighboring diffusion gradients, there may be at most one component exceeding the first threshold.

In some embodiments, according to the list, if a component in the specific direction of a first diffusion gradient exceeds the first threshold, the component in the specific direction of a second diffusion gradient may be below the second threshold. The second diffusion gradient may be next to the first diffusion gradient in the list.

Merely by way of example, the processing device 140 may generate, based on the process 800, a list by arranging n diffusion gradients. The processing device 140 may cause the MRI scanner 110 to perform m×n scans tom slices (e.g., slice 1, slice 2, . . . , slice j, . . . , slice m) by applying, in the scan order described in FIG. 7A according to the list, the n diffusion gradients to the m slices to improve the performance of the gradient amplifier in a specific direction, e.g., the readout direction.

In 810, the processing device 140 (e.g., the control module 520) may generate a first arrangement result by arranging the n diffusion gradients in a descending order based on the components in the readout direction of the n diffusion gradients. The first arrangement result may be denoted as {d1, d2, . . . , di, . . . , dn}, wherein d1-dn refer to the serial numbers of the n diffusion gradient, respectively, d1 refers to the diffusion gradient whose first component has a maximum absolute value of strength among d1-dn, and dn refers to the diffusion gradient whose first component has a minimum absolute value of strength among d1-dn.

In 820, the processing device 140 (e.g., the control module 520) may generate a second arrangement result based on the first arrangement result. Merely by way of example, among the first arrangement result {d1, d2, . . . , di, . . . , dn}, the processing device 140 may invert the order of the diffusion gradients whose serial numbers are even. For example, n=8. The processing device 140 may invert the order of the diffusion gradients (e.g., d2, d4, d6, and d8) whose serial numbers are even, denoted as {d1, d8, d3, d6, d5, d4, d7, d2}. The processing device 140 may generate the second arrangement result by re-numbering the diffusion gradients in {d1, d8, d3, d6, d5, d4, d7, d2}. The second arrangement result may be denoted as {L1, L2, . . . , Li, . . . , Ln}. For example, the processing device 140 may generate the second arrangement result based on Equation (3) below:

$$Li = \begin{cases} di, & i \text{ is an odd number} \\ d(n-i+2), & i \text{ is an even number} \end{cases} \quad (3)$$

In 830, the processing device 140 (e.g., the control module 520) may generate a third arrangement result by filling, based on the second arrangement result, the n diffusion gradients into a list in the format of an m×n matrix. For two components in the readout direction of two neighboring diffusion gradients (from left to right (or vice versa) and/or from top to bottom (or vice versa) of the list), there may be at most one component exceeding the first threshold.

Merely by way of example, the user of the MRI system 100 may define 16 non-colinear diffusion gradients (e.g., A1-A16) in 16 different directions to be applied and 19 slices (e.g., slices 1-19) to be scanned. The 16 diffusion gradients A1-A16 and their own components in the readout (RO) direction, the phase-encoding (PE) direction, and the slice-selection (SS) direction are shown in Table 1 below:

TABLE 1

|  | RO | PE | SS |
| --- | --- | --- | --- |
| A1 | −0.235244599218629 | 0.238133957055610 | 0.942312154774363 |
| A2 | 0.407381158250509 | 0.743974094788493 | 0.529663230917643 |
| A3 | −0.0230242282269156 | 0.999733826000353 | 0.00147039629022677 |
| A4 | −0.798689467489199 | −0.318007000269054 | 0.510848981893571 |
| A5 | −0.321987176804349 | −0.341401145000601 | 0.883045591215903 |
| A6 | 0.202703961700575 | −0.362247586640581 | 0.909773481936562 |
| A7 | 0.827894314717480 | 0.187963595496144 | 0.528451218587521 |
| A8 | 0.296288353128533 | 0.202420578673613 | 0.933401907609911 |
| A9 | −0.198059541814842 | 0.799387997590308 | 0.567231211416168 |
| A10 | −0.768930133879847 | 0.298538662789428 | 0.565350436482913 |
| A11 | −0.947815878973681 | 0.317622801353776 | 0.0275828864611423 |
| A12 | −0.966069962643788 | −0.257939017894280 | 0.0132774366940217 |
| A13 | −0.540565708538346 | −0.839694728480827 | 0.0519757415911179 |
| A14 | 0.0128162195440338 | −0.861394470254960 | 0.507774862641679 |
| A15 | 0.547610502144171 | −0.836732134543416 | 0.00143977908958344 |
| A16 | 0.722900312122695 | −0.429709963416697 | 0.541077153531113 |

Traditionally, the processing device 140 may cause the MRI scanner 110 to perform scans to slices 1-19 by applying diffusion gradients A1-A16 to slices 1-19 according to Table 2. As shown in Table 1, the absolute values of the components in the readout direction of A10-A12 are relatively large. According to the order from top to bottom (or vice versa) in Table 2, if the processing device 140 causes the MRI scanner 110 to successively perform 19 scans to slices 1-19 by applying diffusion gradient A12 to slices 1-19, the X gradient amplifier 204 may continuously work at a higher power for an extended period of time. According to the order from left to right (or vice versa) in Table 2, if the processing device 140 causes the MRI scanner 110 to perform 16 scans to slice 1 by successively applying diffusion gradients A1-A16, the X gradient amplifier 204 may continuously work at a higher power for 3 scans when diffusion gradients A10-A12 are successively applied to slice 1.

TABLE 2

| Slice1 | A1 | A2 | A3 | A4 | A5 | A6 | A7 | A8 | A9 | A10 | A11 | A12 | A13 | A14 | A15 | A16 |
| --- | --- | --- | --- | --- | --- | --- | --- | --- | --- | --- | --- | --- | --- | --- | --- | --- |
| Slice2 | A1 | A2 | A3 | A4 | A5 | A6 | A7 | A8 | A9 | A10 | A11 | A12 | A13 | A14 | A15 | A16 |
| Slice3 | A1 | A2 | A3 | A4 | A5 | A6 | A7 | A8 | A9 | A10 | A11 | A12 | A13 | A14 | A15 | A16 |
| Slice4 | A1 | A2 | A3 | A4 | A5 | A6 | A7 | A8 | A9 | A10 | A11 | A12 | A13 | A14 | A15 | A16 |
| Slice5 | A1 | A2 | A3 | A4 | A5 | A6 | A7 | A8 | A9 | A10 | A11 | A12 | A13 | A14 | A15 | A16 |
| Slice6 | A1 | A2 | A3 | A4 | A5 | A6 | A7 | A8 | A9 | A10 | A11 | A12 | A13 | A14 | A15 | A16 |
| Slice7 | A1 | A2 | A3 | A4 | A5 | A6 | A7 | A8 | A9 | A10 | A11 | A12 | A13 | A14 | A15 | A16 |
| Slice8 | A1 | A2 | A3 | A4 | A5 | A6 | A7 | A8 | A9 | A10 | A11 | A12 | A13 | A14 | A15 | A16 |

TABLE 2-continued

| | | | | | | | | | | | | | | | | |
|---|---|---|---|---|---|---|---|---|---|---|---|---|---|---|---|---|
| Slice9  | A1 | A2 | A3 | A4 | A5 | A6 | A7 | A8 | A9 | A10 | A11 | A12 | A13 | A14 | A15 | A16 |
| Slice10 | A1 | A2 | A3 | A4 | A5 | A6 | A7 | A8 | A9 | A10 | A11 | A12 | A13 | A14 | A15 | A16 |
| Slice11 | A1 | A2 | A3 | A4 | A5 | A6 | A7 | A8 | A9 | A10 | A11 | A12 | A13 | A14 | A15 | A16 |
| Slice12 | A1 | A2 | A3 | A4 | A5 | A6 | A7 | A8 | A9 | A10 | A11 | A12 | A13 | A14 | A15 | A16 |
| Slice13 | A1 | A2 | A3 | A4 | A5 | A6 | A7 | A8 | A9 | A10 | A11 | A12 | A13 | A14 | A15 | A16 |
| Slice14 | A1 | A2 | A3 | A4 | A5 | A6 | A7 | A8 | A9 | A10 | A11 | A12 | A13 | A14 | A15 | A16 |
| Slice15 | A1 | A2 | A3 | A4 | A5 | A6 | A7 | A8 | A9 | A10 | A11 | A12 | A13 | A14 | A15 | A16 |
| Slice16 | A1 | A2 | A3 | A4 | A5 | A6 | A7 | A8 | A9 | A10 | A11 | A12 | A13 | A14 | A15 | A16 |
| Slice17 | A1 | A2 | A3 | A4 | A5 | A6 | A7 | A8 | A9 | A10 | A11 | A12 | A13 | A14 | A15 | A16 |
| Slice18 | A1 | A2 | A3 | A4 | A5 | A6 | A7 | A8 | A9 | A10 | A11 | A12 | A13 | A14 | A15 | A16 |
| Slice19 | A1 | A2 | A3 | A4 | A5 | A6 | A7 | A8 | A9 | A10 | A11 | A12 | A13 | A14 | A15 | A16 |

According to some embodiments of the present disclosure, the processing device 140 may arrange A1-A16 based on the process 800. For example, the processing device 140 may generate the second arrangement result Table 3 by arranging A1-A16 based on operations 810-820.

TABLE 3

| | RO | PE | SS |
|---|---|---|---|
| L1  | 0.0128162195440338  | −0.861394470254960 | 0.507774862641679   |
| L2  | −0.966069962643788  | −0.257939017894280 | 0.0132774366940217  |
| L3  | −0.198059541814842  | 0.799387997590308  | 0.567231211416168   |
| L4  | 0.827894314717480   | 0.187963595496144  | 0.528451218587521   |
| L5  | −0.235244599218629  | 0.238133957055610  | 0.942312154774363   |
| L6  | −0.768930133879847  | 0.298538662789428  | 0.565350436482913   |
| L7  | −0.321987176804349  | −0.341401145000601 | 0.883045591215903   |
| L8  | 0.547610502144171   | −0.836732134543416 | 0.00143977908958344 |
| L9  | −0.540565708538346  | −0.839694728480827 | 0.0519757415911179  |
| L10 | 0.407381158250509   | 0.743974094788493  | 0.529663230917643   |
| L11 | 0.722900312122695   | −0.429709963416697 | 0.541077153531113   |
| L12 | 0.296288353128533   | 0.202420578673613  | 0.933401907609911   |
| L13 | −0.798689467489199  | −0.318007000269054 | 0.510848981893571   |
| L14 | 0.202703961700575   | −0.362247588640581 | 0.909773481936562   |
| L15 | −0.947815878973681  | 0.317622801353776  | 0.0275828864611423  |
| L16 | −0.0230242282269156 | 0.999733826000353  | 0.00147039629022677 |

The processing device 140 may generate the third arrangement result by filling L1-L16 into a list in the format of a 16×19 matrix based on operation 830. For two components in the readout direction of two neighboring diffusion gradients (whether from left to right (or vice versa) and/or from top to bottom (or vice versa) of the 16×19 matrix), there may be at most one component exceeding the first threshold.

In some embodiments, the processing device 140 may cause the MRI scanner 110 to perform 19 scans by applying, according to the order from top to bottom (or vice versa) in column 1 of the 16×19 matrix, the 16 diffusion gradients to the 19 slices. Then the processing device 140 may cause the MRI scanner 110 to perform 19 scans by applying, according to the order from top to bottom (or vice versa) in column 2 of the 16×19 matrix, the 16 diffusion gradients to the 19 slices, and the like, until the processing device 140 causes the MRI scanner 110 to perform 19 scans by applying, according to the order from top to bottom (or vice versa) in column 16 of the 16×19 matrix, the 16 diffusion gradients to the 19 slices.

In some embodiments, the processing device 140 may cause the MRI scanner 110 to perform 16 scans by applying, according to the order from left to right (or vice versa) in row 1 of the 16×19 matrix, the 16 diffusion gradients to slice 1. Then the processing device 140 may cause the MRI scanner 110 to perform 16 scans by applying, according to the order from left to right (or vice versa) in row 2 of the 16×19 matrix, the 16 diffusion gradients to slice 2, and the like, until the processing device 140 causes the MRI scanner 110 to perform 16 scans by applying, according to the order from left to right (or vice versa) in the row of slice 19 of the 16×19 matrix, the 16 diffusion gradients to slice 19.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 9 is a flowchart illustrating an exemplary process for determining a diffusion gradient for a scan according to some embodiments of the present disclosure. In some embodiments, the process 900 may be implemented in the MRI system 100 illustrated in FIG. 1. For example, the process 900 may be stored in a storage medium (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 900 presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

Merely by way of example, to perform EPI-DTI, during the scanning process, the polarity of the applied frequency-encoding gradients (also referred to as readout gradients) may be switched continuously. Echoes may be collected with each switch of the polarity of the readout gradients. In this case, the workload of the gradient amplifier for the readout gradient (e.g., the X gradient amplifier 204) may be higher than the workload of the gradient amplifiers for the phase-encoding gradient and the slice-selection gradient (e.g., the Y gradient amplifier 205 and the Z gradient amplifier 206). Therefore, in the process 900, when determining a diffusion gradient for each scan, the processing device 140 may consider only the component in the readout direction (the first component) to improve the stability of the X gradient amplifier 204.

In 910, the processing device 140 (e.g., the control module 520) may obtain a first diffusion gradient applied in a first scan.

In 920, the processing device 140 (e.g., the control module 520) may determine whether the first component of the first diffusion gradient exceeds the first threshold. In response to a determination that the first component of the first diffusion gradient exceeds the first threshold, the process 900 may proceed to operation 930, in which the processing device 140 (e.g., the control module 520) may select a second diffusion gradient applied in a second scan. The first component of the second diffusion gradient may be below the second threshold. The second scan may be performed next to the first scan. In response to a determination that the first component of the first diffusion gradient does not exceed the first threshold, the process 900 may proceed to operation 940, in which the processing device 140 (e.g., the control module 520) may select a second diffusion gradient applied in the second scan without considering the first component of the second diffusion gradient.

In some embodiments, the processing device 140 may determine a diffusion gradient for each scan by repeating the process 900.

In some embodiments, when determining a diffusion gradient for each scan based on the process 900, the processing device 140 may consider only the characteristic of the gradient amplifier in the readout direction (e.g., the X gradient amplifier 204).

In some embodiments, the processing device 140 may determine a diffusion gradient for each scan based on the process 900 before all of the plurality of scans are performed to the object. In some embodiments, the processing device 140 may determine a diffusion gradient for each scan based on the process 900 real time during the scanning process of the plurality of scans. For example, after the first scan is completed and before the second scan begins, the processing device 140 may determine a diffusion gradient for the second scan based on the process 900.

FIG. 10 is a flowchart illustrating an exemplary process for determining a diffusion gradient for a scan according to some embodiments of the present disclosure. In some embodiments, the process 1000 may be implemented in the MRI system 100 illustrated in FIG. 1. For example, the process 1000 may be stored in a storage medium (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 1000 presented below are intended to be illustrative. In some embodiments, the process 1000 may be accomplished with one or more additional operations not described, and/or without one or more of the operations discussed. Additionally, the order in which the operations of the process 1000 as illustrated in FIG. 9 and described below is not intended to be limiting.

Compared to process 900, in the process 1000, when determining a diffusion gradient for each scan, the processing device 140 may consider at least one of the first component, the second component, and the third component to improve the stability of at least one of the X gradient amplifier 204, the Y gradient amplifier 205, and the Z gradient amplifier 206.

In 1010, the processing device 140 (e.g., the control module 520) may obtain a first diffusion gradient applied in a first scan.

In 1020, the processing device 140 (e.g., the control module 520) may determine whether at least one of the first component, the second component, and the third component of the first diffusion gradient exceeds the first threshold. In response to a determination that at least one of the first component, the second component, and the third component of the first diffusion gradient exceeds the first threshold, the process 1000 may proceed to operation 1030, in which the processing device 140 (e.g., the control module 520) may select a second diffusion gradient applied in a second scan. The at least one of the first component, the second component, and the third component of the second diffusion gradient may be below the second threshold. The second scan may be performed next to the first scan. For example, in response to a determination that the first component and the second component of the first diffusion gradient exceed the first threshold, for the second scan performed next to the first scan, the processing device 140 may select a second diffusion gradient of which the first component and the second component are below the second threshold.

In response to a determination that none of the first component, the second component, and the third component of the first diffusion gradient exceeds the first threshold, the process 1000 may proceed to operation 1040, in which the processing device 140 (e.g., the control module 520) may select a second diffusion gradient applied in the second scan without considering the first component, the second component, and the third component of the second diffusion gradient.

In some embodiments, the processing device 140 may determine a diffusion gradient for each scan by repeating the process 1000.

In some embodiments, when determining a diffusion gradient for each scan based on the process 1000, the processing device 140 may consider the characteristic of at least one of the X gradient amplifier 204, the Y gradient amplifier 205, and the Z gradient amplifier 206.

In some embodiments, the processing device 140 may determine a diffusion gradient for each scan based on the process 1000 before all of the plurality of scans are performed to the object. In some embodiments, the processing device 140 may determine a diffusion gradient for each scan based on the process 1000 real time during the scanning process of the plurality of scans. For example, after the first scan is completed and before the second scan begins, the processing device 140 may determine a diffusion gradient for the second scan based on the process 1000.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

I claim:

1. A system for magnetic resonance imaging (MRI), comprising:
    an imaging device configured to scan an object;
    at least one storage device including a set of instructions; and
    at least one processor in communication with the at least one storage device and the imaging device, wherein when executing the set of instructions, the at least one processor is directed to cause the system to perform operations including:
        obtaining one or more scan parameters, wherein the one or more scan parameters include information of a plurality of diffusion gradients; and
        causing, based on the one or more scan parameters, the imaging device to perform a plurality of scans to one or more slices of the object by applying the plurality of diffusion gradients to the one or more slices, wherein for two components in a specific direction of the plurality of diffusion gradients, there is at most one component whose energy exceeds a first threshold, the two components being respectively applied in any two successive scans of the plurality of scans, the specific direction being one of a readout direction, a phase-encoding direction, or a slice-selection direction, the first threshold being less than energy of one of the plurality of diffusion gradients, the energy of the one of the plurality of diffusion gradients relating to a duration and strength of the one of the plurality of diffusion gradients.

2. A system for magnetic resonance imaging (MRI), comprising:
an imaging device configured to scan an object;
at least one storage device including a set of instructions; and
at least one processor in communication with the at least one storage device and the imaging device, wherein when executing the set of instructions, the at least one processor is directed to cause the system to perform operations including:
obtaining one or more scan parameters, wherein the one or more scan parameters includes information of a plurality of diffusion gradients; and
causing, based on the one or more scan parameters, the imaging device to perform a plurality of scans by applying the plurality of diffusion gradients to one or more slices of the object, wherein directions of two of the plurality of diffusion gradients that are respectively applied in two successive scans of the plurality of scans are different.

3. A method for magnetic resonance imaging (MRI) implemented on a machine including at least one storage device and at least one processor, the method comprising:
obtaining one or more scan parameters, wherein the one or more scan parameters include information of a plurality of diffusion gradients; and
causing, based on the one or more scan parameters, an imaging device to perform a plurality of scans to one or more slices of an object by applying the plurality of diffusion gradients to the one or more slices, wherein for two components in a specific direction of the plurality of diffusion gradients, there is at most one component whose energy exceeds a first threshold, the two components being respectively applied in any two successive scans of the plurality of scans, the specific direction being one of a readout direction, a phase-encoding direction, or a slice-selection direction, the first threshold being less than energy of one of the plurality of diffusion gradients, the energy of the one of the plurality of diffusion gradients relating to a duration and strength of the one of the plurality of diffusion gradients.

4. The system of claim 1, wherein if the energy of a component in the specific direction of a first diffusion gradient applied in a first scan exceeds the first threshold, the energy of a component in the specific direction of a second diffusion gradient applied in a second scan is below a second threshold, the second scan being performed next to the first scan, the first threshold being greater than the second threshold.

5. The system of claim 1, wherein to cause, based on the one or more scan parameters, the imaging device to perform the plurality of scans to the one or more slices of the object, the at least one processor is directed to cause the system to perform the operations including:
determining a list by arranging the plurality of diffusion gradients such that if the energy of a component in the specific direction of a first diffusion gradient applied in a first scan exceeds the first threshold, the energy of a component in the specific direction of a second diffusion gradient applied in a second scan is below a second threshold that is less than the first threshold, the second scan being performed next to the first scan; and
causing the imaging device to perform the plurality of scans by applying the plurality of diffusion gradients to the one or more slices based on the list.

6. The system of claim 5, wherein the first threshold is in a range of 70%-90% of the energy of the one of the plurality of diffusion gradients, and the second threshold is in a range of 30%-50% of the energy of the one of the plurality of diffusion gradients.

7. The system of claim 1, wherein the specific direction is the readout direction.

8. The system of claim 1, wherein to cause, based on the one or more scan parameters, the imaging device to perform the plurality of scans to the one or more slices of the object, the at least one processor is directed to cause the system to perform the operations including:
causing, based on the one or more scan parameters, the imaging device to perform a third scan of the plurality of scans by applying a third diffusion gradient of the plurality of diffusion gradients to a third slice of the one or more slices of the object; and
causing, based on the one or more scan parameters, the imaging device to perform, immediately after the third scan, a fourth scan of the plurality of scans by applying a fourth diffusion gradient of the plurality of diffusion gradients to a fourth slice of the one or more slices of the object, wherein the third slice is different from the fourth slice.

9. The system of claim 8, wherein the fourth slice is next to the third slice.

10. The system of claim 1, wherein to cause, based on the one or more scan parameters, the imaging device to perform the plurality of scans to the one or more slices of the object, the at least one processor is directed to cause the system to perform the operations including:
causing, based on the one or more scan parameters, the imaging device to perform a third scan of the plurality of scans by applying a third diffusion gradient of the plurality of diffusion gradients to a third slice of the one or more slices of the object; and
causing, based on the one or more scan parameters, the imaging device to perform, immediately after the third scan, a fourth scan of the plurality of scans by applying a fourth diffusion gradient of the plurality of diffusion gradients to the third slice.

11. The system of claim 1, wherein when executing the set of instructions, the at least one processor is directed to cause the system to perform operations including:
obtaining imaging data related to the one or more slices based on the plurality of scans; and
generating one or more images based on the imaging data.

12. The method of claim 3, wherein if the energy of a component in the specific direction of a first diffusion gradient applied in a first scan exceeds the first threshold, the energy of a component in the specific direction of a second diffusion gradient applied in a second scan is below a second threshold, the second scan being performed next to the first scan, the first threshold being greater than the second threshold.

13. The method of claim 3, wherein the causing, based on the one or more scan parameters, the imaging device to perform the plurality of scans to the one or more slices of the object includes:
determining a list by arranging the plurality of diffusion gradients such that if the energy of a component in the specific direction of a first diffusion gradient applied in a first scan exceeds the first threshold, the energy of a component in the specific direction of a second diffusion gradient applied in a second scan is below a second threshold that is less than the first threshold, the second scan being performed next to the first scan; and causing the imaging device to perform the plurality of scans by applying the plurality of diffusion gradients to the one or more slices based on the list.

14. The method of claim 12, wherein the first threshold is in a range of 70%-90% of the energy of the one of the plurality of diffusion gradients, and the second threshold is in a range of 30%-50% of the energy of the one of the plurality of diffusion gradients.

15. The method of claim 3, wherein the specific direction is the readout direction.

16. The method of claim 3, wherein the causing, based on the one or more scan parameters, the imaging device to perform the plurality of scans to the one or more slices of the object includes:
   causing, based on the one or more scan parameters, the imaging device to perform a third scan of the plurality of scans by applying a third diffusion gradient of the plurality of diffusion gradients to a third slice of the one or more slices of the object; and
   causing, based on the one or more scan parameters, the imaging device to perform, immediately after the third scan, a fourth scan of the plurality of scans by applying a fourth diffusion gradient of the plurality of diffusion gradients to a fourth slice of the one or more slices of the object, wherein the third slice is different from the fourth slice.

17. The method of claim 16, wherein the fourth slice is next to the third slice.

18. The method of claim 3, wherein the causing, based on the one or more scan parameters, the imaging device to perform the plurality of scans to the one or more slices of the object includes:
   causing, based on the one or more scan parameters, the imaging device to perform a third scan of the plurality of scans by applying a third diffusion gradient of the plurality of diffusion gradients to a third slice of the one or more slices of the object; and
   causing, based on the one or more scan parameters, the imaging device to perform, immediately after the third scan, a fourth scan of the plurality of scans by applying a fourth diffusion gradient of the plurality of diffusion gradients to the third slice.

19. The method of claim 3, further comprising:
   obtaining imaging data related to the one or more slices based on the plurality of scans; and
   generating one or more images based on the imaging data.

* * * * *